(12) United States Patent
Ewers et al.

(10) Patent No.: US 10,675,114 B2
(45) Date of Patent: Jun. 9, 2020

(54) ACCESS SHEATH FOR BRAIN SURGERY

(71) Applicant: SPIWay LLC, Carlsbad, CA (US)

(72) Inventors: Richard C. Ewers, Carlsbad, CA (US); Eugene Chen, Carlsbad, CA (US); Stephanie Frimond, Carlsbad, CA (US)

(73) Assignee: SPIWay LLC, Carlsbad, CA (US)

( * ) Notice: Subject to any disclaimer, the term of this patent is extended or adjusted under 35 U.S.C. 154(b) by 289 days.

(21) Appl. No.: 15/716,214

(22) Filed: Sep. 26, 2017

(65) Prior Publication Data

US 2018/0085182 A1  Mar. 29, 2018

Related U.S. Application Data

(60) Provisional application No. 62/399,820, filed on Sep. 26, 2016.

(51) Int. Cl.
*A61B 90/10* (2016.01)
*A61B 17/34* (2006.01)

(52) U.S. Cl.
CPC .......... *A61B 90/10* (2016.02); *A61B 17/3421* (2013.01); *A61B 17/3423* (2013.01); *A61B 17/3431* (2013.01); *A61B 17/3439* (2013.01); *A61B 2017/347* (2013.01); *A61B 2090/103* (2016.02)

(58) Field of Classification Search
CPC . A61B 17/34; A61B 17/3415; A61B 17/3421; A61B 17/3431; A61B 17/3423; A61B 17/3439; A61B 2017/3445; A61B 2017/347; A61B 2090/103
See application file for complete search history.

(56) References Cited

U.S. PATENT DOCUMENTS

| 6,099,505 A | 8/2000 | Ryan et al. |
|---|---|---|
| 2006/0212062 A1 | 9/2006 | Farascioni |
| 2008/0097506 A1* | 4/2008 | Criscuolo .......... A61B 17/0218 606/190 |
| 2010/0057009 A1 | 3/2010 | McQueen et al. |
| 2011/0144622 A1 | 6/2011 | Orth et al. |
| 2017/0135687 A1* | 5/2017 | Pacak ..................... A61B 17/34 |

FOREIGN PATENT DOCUMENTS

WO    2005037079 A2    4/2005

OTHER PUBLICATIONS

International Search Report and Written Opinion for International Application No. PCT/US2017/053525; dated Jan. 11, 2018; 14 pages.

* cited by examiner

*Primary Examiner* — Ashley L Fishback
(74) *Attorney, Agent, or Firm* — Perkins Coie LLP; Kenneth H. Ohriner

(57) ABSTRACT

A surgical sheath system for performing surgery of the head includes a flexible tubular braided sheath which is radially expandable. An expansion tube is insertable into the sheath to radially expand the sheath. A locking assembly includes tube position shift means, such as a cap threaded onto a flange, with a washer contained in a recess in the flange, the recess having an inside diameter greater than an outside diameter of the washer. When unlocked, the expansion tube can be shift horizontally, to access a different area of a surgical site, without moving the locking assembly. A stylet stabilizing assembly may be pivotally or releasably attached to the locking assembly.

14 Claims, 14 Drawing Sheets

ACCESS SHEATH FOR BRAIN SURGERY

This application claims priority to U.S. Provisional Patent Application No. 62/399,820 filed Sep. 26, 2016, incorporated herein by reference.

BACKGROUND OF THE INVENTION

A recent evolution in neurosurgical technologies has led to a way to treat the most serious kinds of brain tumors while preserving brain function. Latest technology uses a large bore access tube, advanced imaging of tracts in the brain and a computerized brain navigation system, which allows physicians to navigate the brain with unprecedented clarity to target and remove deep-seated brain tumors, abscesses and hemorrhages with much less disruption of tissue than with microscopic surgical techniques. While individual technologies have been available for more than a decade, they have primarily been used independent of one another. Neurosurgery has now evolved by using a "6 Pillar Approach". The Pillars of the approach include: brain imaging, neuro-navigation, access, high-definition optics, resection (removal) of the abnormality, and tissue collection for regenerative medicine options.

This procedure is an improvement to traditional open surgery because a small opening is created to access deep in the brain, so less of the brain is exposed, and there is less disruption to the brain tissue.

The currently used rigid large access tube devices provide access and visualization of lesions in the subcortical space of the brain, and decrease trauma to the brain tissue. These devices typically have an obturator uniquely designed with a sharp tip that is intended to displace tissue of the brain during advancement to the targeted abnormality. A rigid sheath remains in the brain after the obturator is removed to serve as a protective portal for surgeons to easily maintain access to the surgical site. Rigid access tube devices do not vary by abnormality type, but rather they are adapted to where the abnormality is located, and they provide a pathway to deep locations within the brain.

The difference from a surgical standpoint is that surgeons using the rigid access devices enter the brain through the sulci, the natural folds of the brain, to displace the critical structures in the white matter to reach the abnormality, thereby potentially reducing tissue damage. While existing minimally invasive approaches use small openings, surgeons using the rigid access devices still cut through the brain's white matter—tissue responsible for any number of cognitive and functional responses—to reach the target abnormality. The rigid access devices attempt to displace white matter but are quite large in diameter.

These rigid access devices attempt to provide atraumatic access to the brain abnormality by navigating through the delicate folds and fibers of the brain. The two-piece system has a clear plastic sheath around a smooth, cylindrical tool with a specially designed tip. The rigid access device enters the brain through an 18 mm diameter opening. Once at the location of the abnormality, the surgeon removes the obturator from the tube, leaving the tube in place to create a portal or narrow corridor through which the surgeon operates.

It would be useful to provide an improvement to neurosurgical access that leverages some of the fundamentals described above but with an even more minimally invasive approach that provides less injury and trauma to the brain's white matter.

It is preferred to navigate through the natural folds of the brain's white matter as opposed to cutting, tearing, or other tissue disruption. This would minimize stress forces and pressure that are harmful to brain tissue.

It would be useful to provide an access sheath for protection of brain matter for neurosurgery. It would provide one or more of the following benefits:

Protecting white matter of the brain from the placement and manipulation of surgical instruments both during the initial placement and during manipulation and exchange Reducing sheer forces and traumatic injury to the brain tissue to protect white matter Providing a guide port to help direct instruments into position Splint and protect white matter to help open and provide access Protect instruments and especially endoscope's image clarity

SUMMARY OF THE INVENTION

A surgical sheath system for performing surgery of the head includes a flexible tubular braided sheath which is radially expandable. An expansion tube is insertable into the sheath to radially expand the sheath. A locking assembly includes tube position shift means, such as a cap threaded onto a flange, with a washer contained in a recess in the flange, the recess having an inside diameter greater than an outside diameter of the washer. When unlocked, the expansion tube can be shift horizontally, to access a different area of a surgical site, without moving the locking assembly. A stylet stabilizing assembly may be pivotally or releasably attached to the locking assembly.

As an improvement to the current access tube devices, which are large bore rigid tubes, would be a smaller flexible radial dilating conical access sheath that can be introduced in a low profile state, potentially of similar size and in conjunction with the insertion of the navigation probe. Upon reaching the target location, the radial dilating conical access sheath is gently radially expanded with the insertion of an expansion tube or by mechanical means without an expansion tube to create surgical access equivalent in diameter of the current rigid access tubes described above. The radial dilation of the tissue provides reduced trauma and stress forces to the white matter of the brain to create a minimally invasive access corridor for surgical tools. The radial dilating conical access sheath is connected to a locking assembly that attaches to the patient's head or an external fixation device. The locking assembly provides the ability to shift horizontally into different positions to allow access to different areas of a surgical site.

BRIEF DESCRIPTION OF THE DRAWINGS

In the drawings, the same reference number indicates the same element in each of the views.

DETAILED DESCRIPTION OF THE DRAWINGS

Figure 1A:
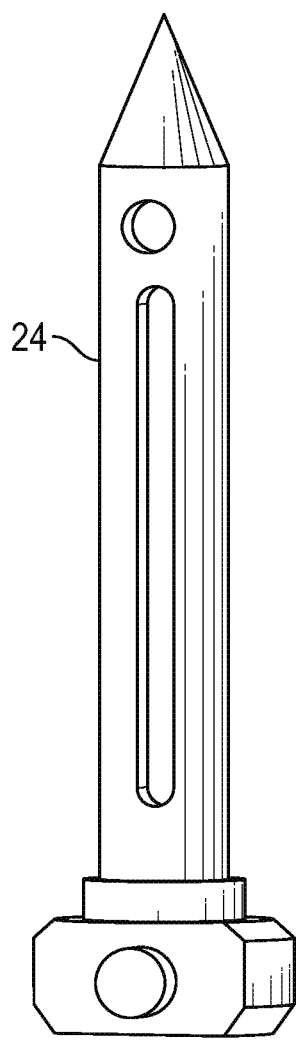
FIGS. 1A and 1B are side views of the prior art rigid tube access device with FIG. 1B showing the tubular rigid tube and FIG. 1A showing the cylindrical pointed obturator of the prior art device.
Figure 1B:
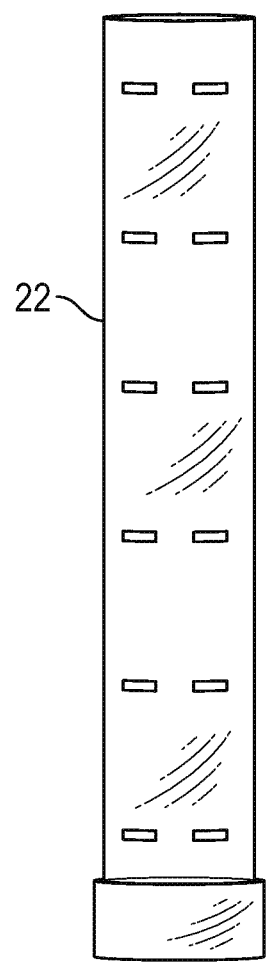

FIG. 1B shows the rigid tube 22 and FIG. 1A shows a rigid pointed obturator 24 of the prior art access system. Obturator 24 is sized to fit snugly in the lumen of the tube 22. Both have a fixed diameter at the maximum working diameter.

Figure 2A:
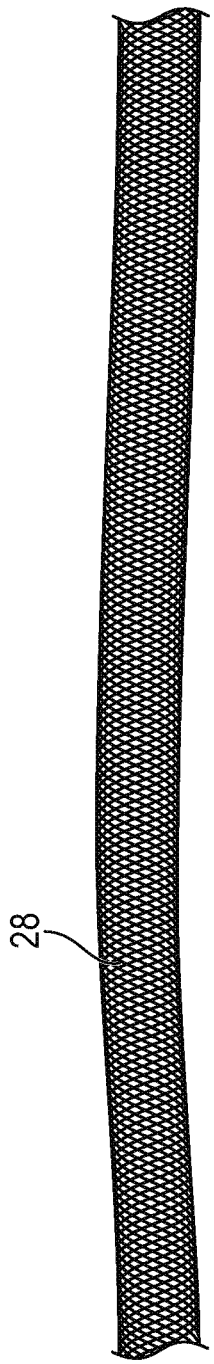
FIG. 2A is a side view of a braid in its natural state.
Figure 2B:
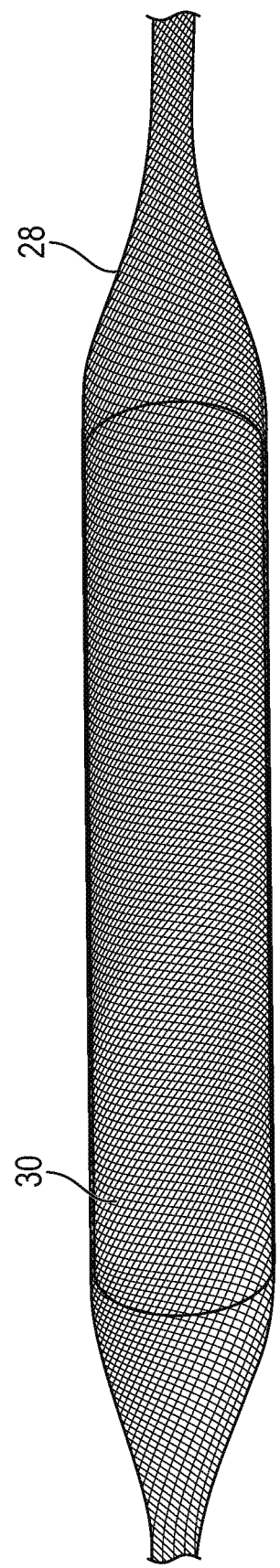
FIG. 2B is a side view of the braid expanded over a mandrel to demonstrate its ability to transform in length and radial direction.

FIG. 2A shows a radial expanding braid 28. FIG. 2B shows the radially expanding braid 28 radially expanded over a mandrel 30. An useful property of the radially expanding braid 28 is its ability to have a variable diameter. A radially expanding braid can be drawn down to a low-profile sleeve by stretching and pulling the monofilaments into a more longitudinal alignment. Conversely, braids can be expanded to a larger tubular diameter by compression and pushing the elements into a more radial directed alignment.

Another useful property of braids, especially if made from thermoelastics, is they can be loaded onto rods or shaped mandrels that cause them to expand or contract to specific diameters or shapes, and then be heat set in an oven. After cooling, the braid will be permanently shaped into a configuration as dictated by the mandrel 30.

Heat setting mandrels can be made of a variety of materials, such as stainless steel. Delrin (acetal homopolymer resin) or Teflon (fluoropolymer resins) makes a useful mandrel 30, especially if it is intended to coat the braid material in a plastic/rubber/silicone dispersion. Heat setting can be done at a variety of temperatures and time. It is dependent on the braid material and the heat capacity of the shaping mandrel 30. For example, braid heat shaped on a solid stainless steel mandrel will require more time to heat and eventually cool compared to braids heat set on a hollow mandrel or a plastic mandrel due to the heat capacity of the mandrel. A useful heat set temperature for nylon or PET braids would be between 120 to 150° C. for one half an hour, followed by cooling to room temperature in ambient conditions or a quench in water. Additionally, braids can be combined with elastomeric coatings to provide a fluid barrier and to help in the maintenance of a shape. The radial expanding braided conical access sheath can be fabricated from the braid material as described above.

After heat setting an elastomeric dispersion can be applied over the heat set radially expanded braid to create a fluid seal and provide additional definition of the intended shape, but still allowing the radially expanding braid 28 to be stretchable to allow radial expansion.

Figure 13A:
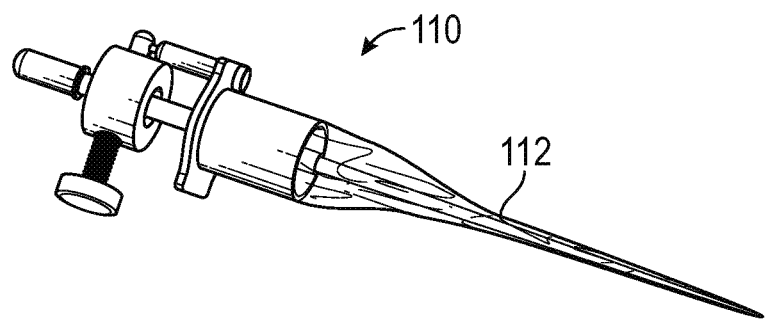
FIG. 13A is a side perspective view of an alternative stylet stabilization assembly embodiment where the radial expanding sheath is constructed from a thin polymer.

In its fabricated low profile configuration, this braided access sheath, or a non-braided sheath FIG. 13A which can be folded into a low-profile configuration, can be positioned on a navigation probe or insertion stylet 50 in its reduced profile to navigate in a minimal invasive manner through the folds of the brain white matter. Once in position, an expansion tube can be inserted. As the expansion tube is inserted within the sheath it causes the sheath to progressively radially dilate in a gradual manner without applying shear forces directly to the tissue. The access sheath acts as a protection sheath against the expansion tube to reduce shearing against the brain white matter and to gradually dilate the tissue as it expands. When fully placed the expansion tube will define an open path through the brain matter to perform operative procedures.

Extracorporeal imaging such as fluoroscopy may be used to view the positioning and progress of the introduction of the stylet/navigation probe. More preferably the stylet is metallic and of a configuration that shows clearly on fluoroscopy or alternate extracorporeal imaging.

Figure 3A:
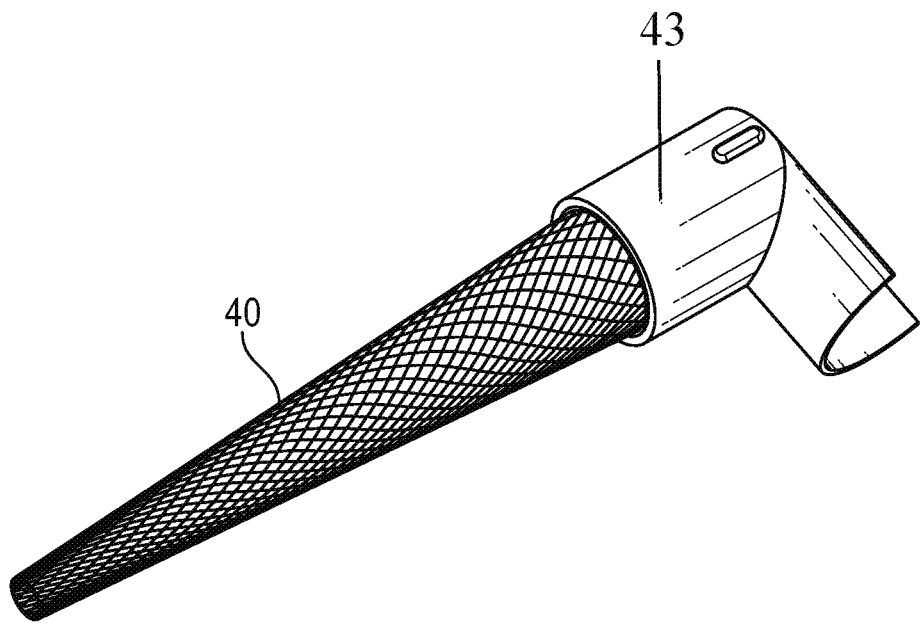
FIG. 3A is a perspective view of a radial expanding braided conical access sheath and FIG. 3B is a perspective view of an insertable expansion tube that induces radial expansion when placed into the access sheath of FIG. 3A.
Figure 3B:
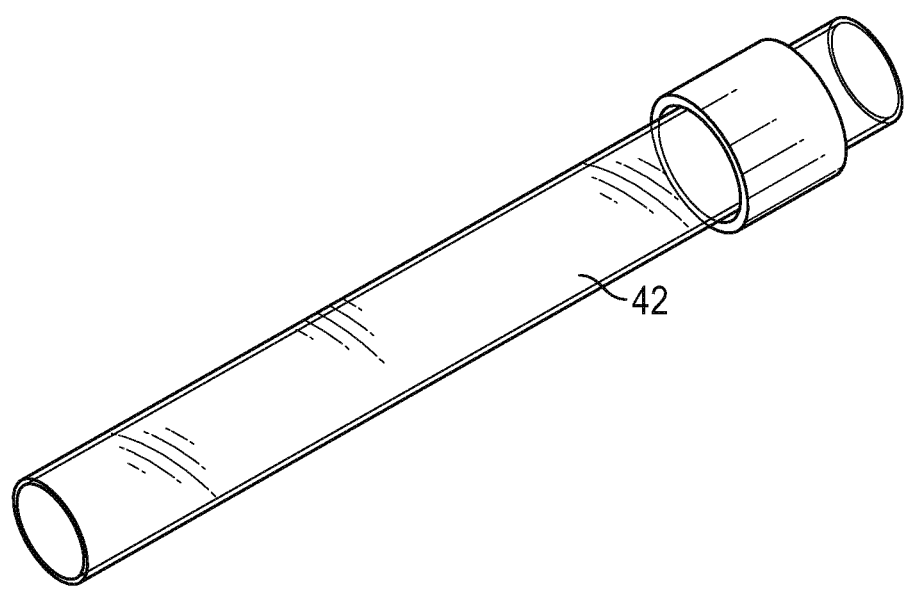

Once in position, the flexible access sheath and expansion tube 40 can be positioned in relation to the cranium either through sewing, tacking, connecting, or positioned by an external fixation device. It would be useful for the access sheath 40 be maintained at the user end with a locking assembly 70. The locking assembly has locations for attachment to the head or external fixation device and allows angulation and/or angular locking of the expansion tube The following images demonstrate the embodiment:

FIG. 3A shows a radially expanding access sheath 40 made from a braided tube 28 and coated in an elastomeric material, shown in its low-profile configuration, prior to placement. The radially expanding access sheath 40 is attached to a locking hub assembly 43. FIG. 3B shows the expansion tube 42 separate from the expanding access sheath 40.

Figure 4:
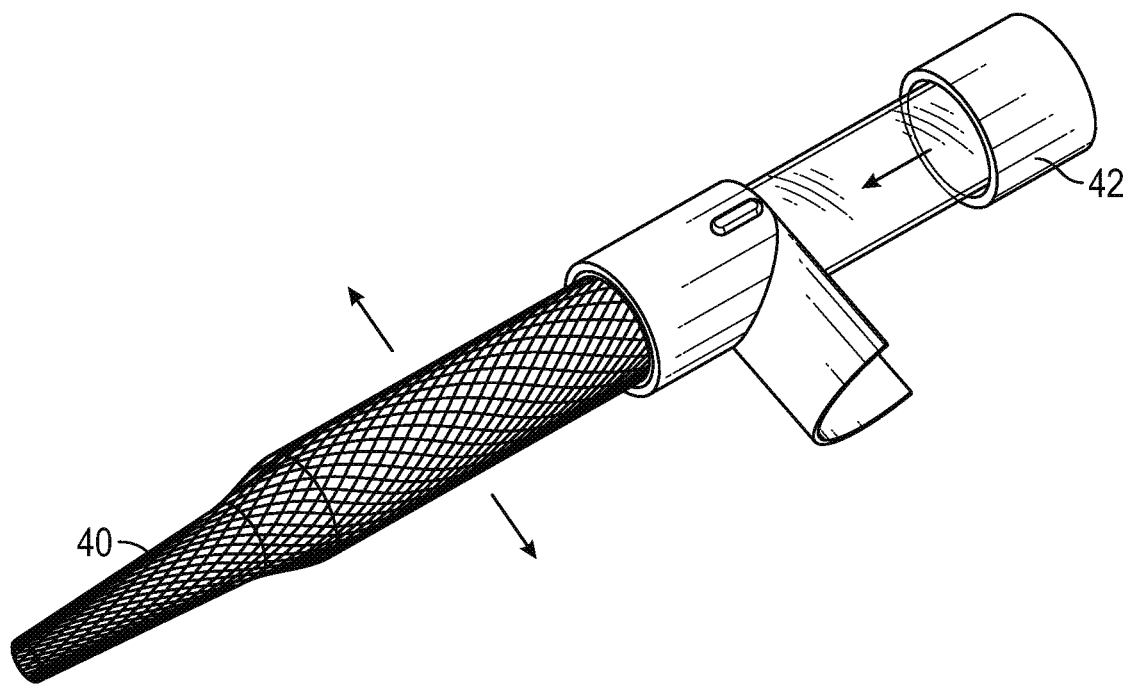
FIG. 4 shows the expansion tube partially placed within the radial dilating access sheath.

FIG. 4 shows the expansion tube 42 partially placed into the access sheath 40. As the expansion tube is inserted the access sheath radially expands. The expansion tube 42 is shown with the access sheath 40 partially expanded.

Figure 5:
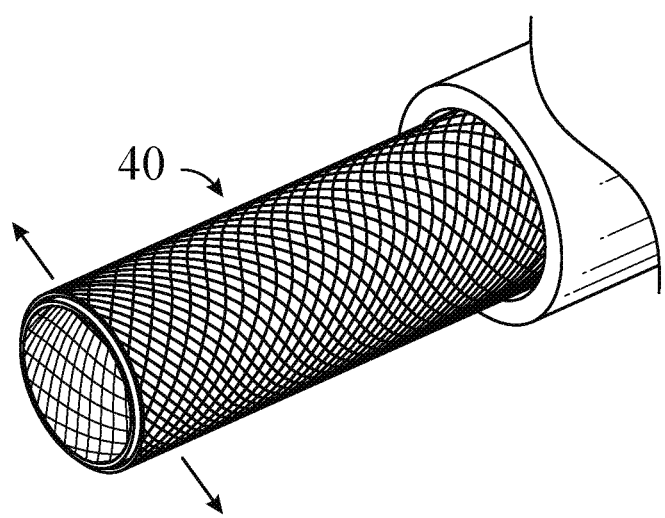
FIG. 5 is a perspective view of the sheath of FIG. 3A fully radially expanded with the expansion tube placed fully within the sheath.

FIG. 5 is a perspective view of the fully expanded access sheath 40 with the expansion tube placed fully within the sheath. The sheath is radially dilated against tissue in an equal circumferential manner spreading forces gently across the entire surface. Trauma to white matter occurs with too much stress forces or pressure. The radial expansion reduces these forces by shielding the expansion tube from the tissue while the access sheath radially expands.

Figure 6A:
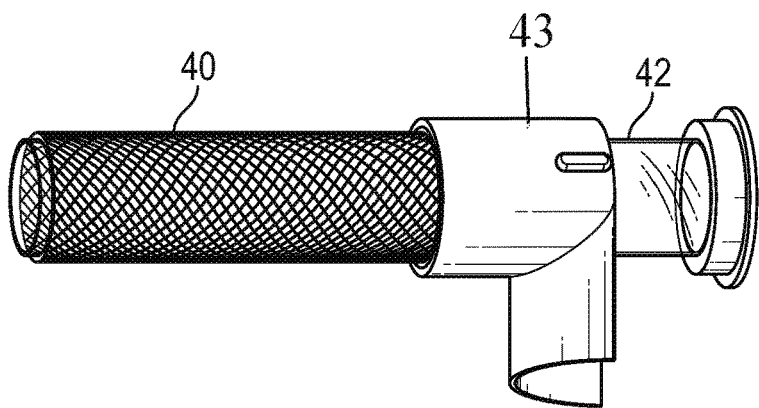
FIG. 6A is a side view of the expansion tube placed within the sheath.
Figure 6B:
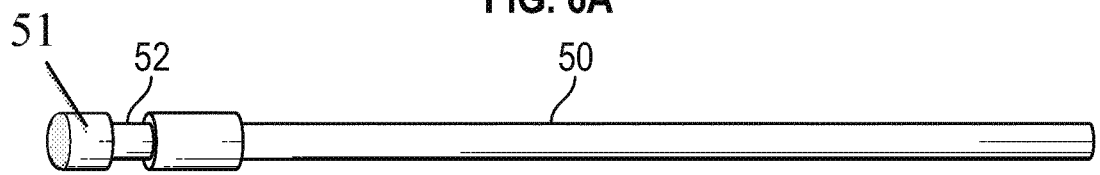
FIG. 6B is a side view of an optional stylet with atraumatic tip and distal annular recess for the access sheath to engage.
Figure 7A:
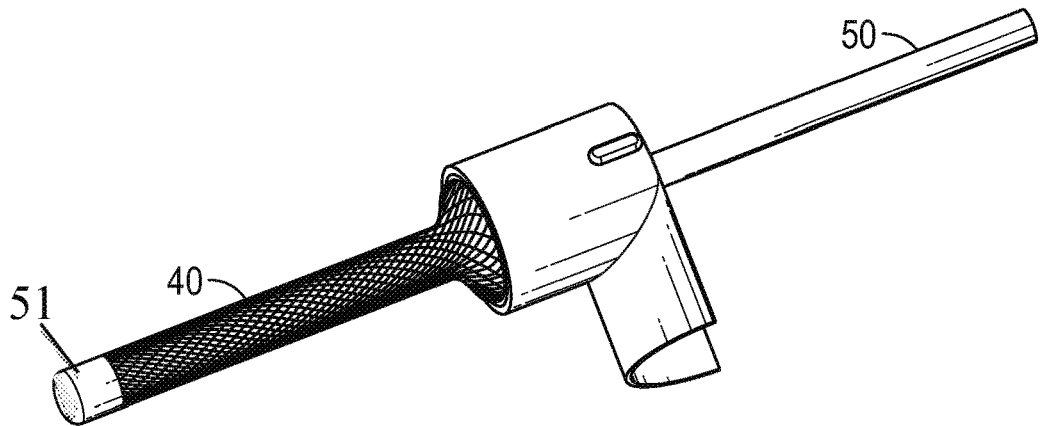
FIG. 7A is a perspective view of the stylet of FIG. 6B placed in the access sheath with sheath's distal end engaged in the annular groove on the stylet.

FIG. 6A is a side view of the fully expanded access sheath 40 permanently connected to a representation of the locking assembly 43. The expansion tube in FIG. 6A is shown to be partially inserted. It may or may not extend past the end of the access sheath. FIG. 6B shows an optional stylet 50 with a distal annular engagement recess 52 for the distal end portion of the access sheath to engage in. The stylet is intended to act as a minimal invasive obturator for the radial expansion access sheath during insertion into the brain white matter. The stylet is shown with a blunt end 51, but could be sharp or tapered as required. The annular recess 52 is of a smaller diameter than the distal end 51, and allows the distal end of the access sheath to engage into the recess so that there is a smooth transition of stylet tip and access sheath. FIG. 7A shows the radially expanding sheath 40 with optional stylet placed and engaged at the distal end with a smooth transition. The stylet 50 can be removed by disengaging the recess by pulling back or it can be freed when the expansion tube 42 is introduced.

Additionally, the stylet could be a navigation probe. Navigation probes are long rigid rods typically between 5 mm and 7 mm in diameter that are used in conjunction with a navigation platform to determine the exact location of the tumor or operating site. The navigation probe is typically placed as the first step in the procedure. One embodiment is for the radially expansion access sheath 40 to hug the navigation probe so that the navigation probe acts as the stylet for placement of the access sheath to the appropriate location. This reduces the number of procedure steps and avoids the requirement for the optional stylet.

Figure 7B:
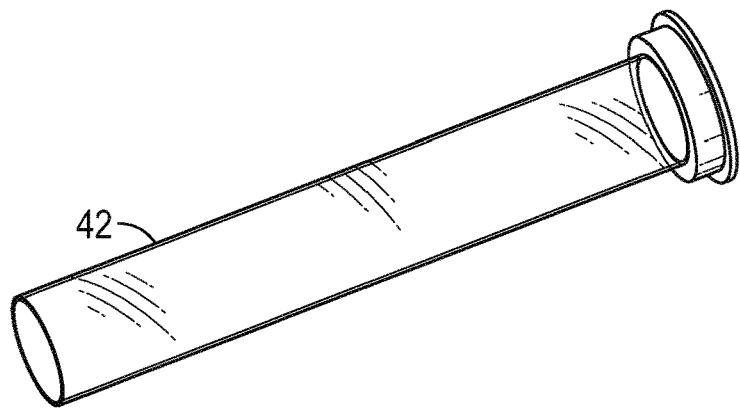
FIG. 7B is a side perspective view of the expansion tube shown in FIG. 3b.

FIG. 7B is a side view of the expansion tube 42, which may be entirely cylindrical, or which may have a conically tapered front end and a cylindrical center and back end. The leading edge of the expansion tube can be smooth with an e.g., a radius of 0.5 to 5 mm, to avoid engaging the access sheath during insertion as well as any tissue on the distal end. In an alternative embodiment, the expansion tube can be non-cylindrical and have a cross sectional oval shape or other geometric shape that can assist surgical access.

Figure 8A:
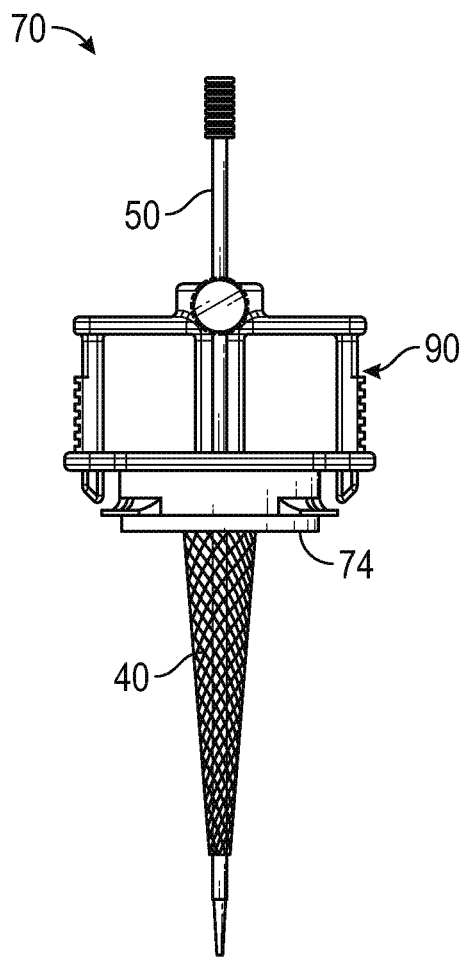
FIG. 8A is a side view of a locking assembly connected to the access sheath.

FIG. 8A, shows a side view of a radial expanding access sheath 40 permanently engaged to a locking assembly 70. The radial expanding access sheath is in its non-expanded state with a stylet 50 or navigation probe temporarily locked in place with the stabilizing structure 90. The radial expanding access sheath may be conical in shape or in closer approximation to the stylet or navigation probe. The total combined assembly can be placed into the patient as one structure.

Figure 8B:
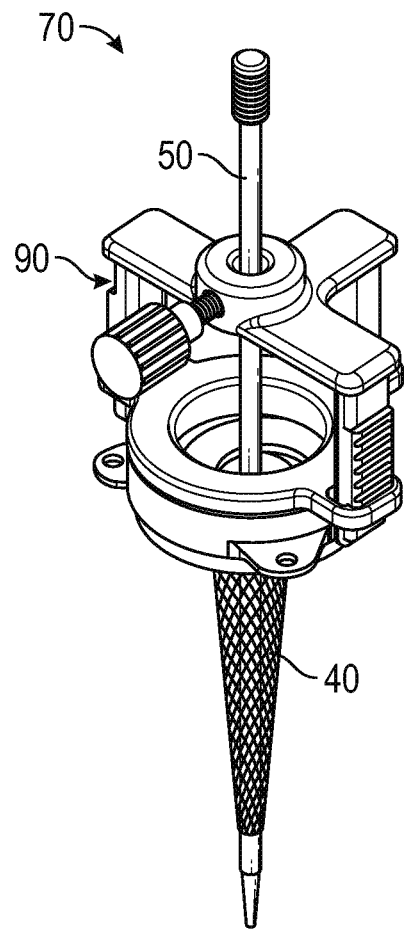
FIG. 8B is a top perspective view of the assembly of FIG. 8A.

FIG. 8B, is a view of the same structure, with a view of the stabilizing structure temporarily holding the stylet in place with a locking screw.

Figure 8C:
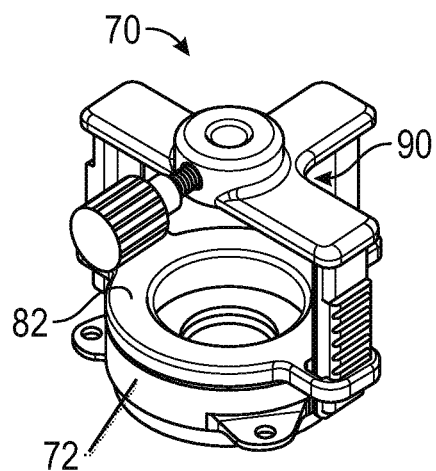
FIG. 8C is a top perspective view of the locking assembly alone, without the stylet and the sheath.

FIG. 8C, shows the locking assembly 70 which serves two purposes. It locks either the stylet 50 or the navigation probe.

Secondly, the locking assembling acts to lock the expansion tube 42 and the access sheath 40 in locked angular configuration.

Figure 8D:
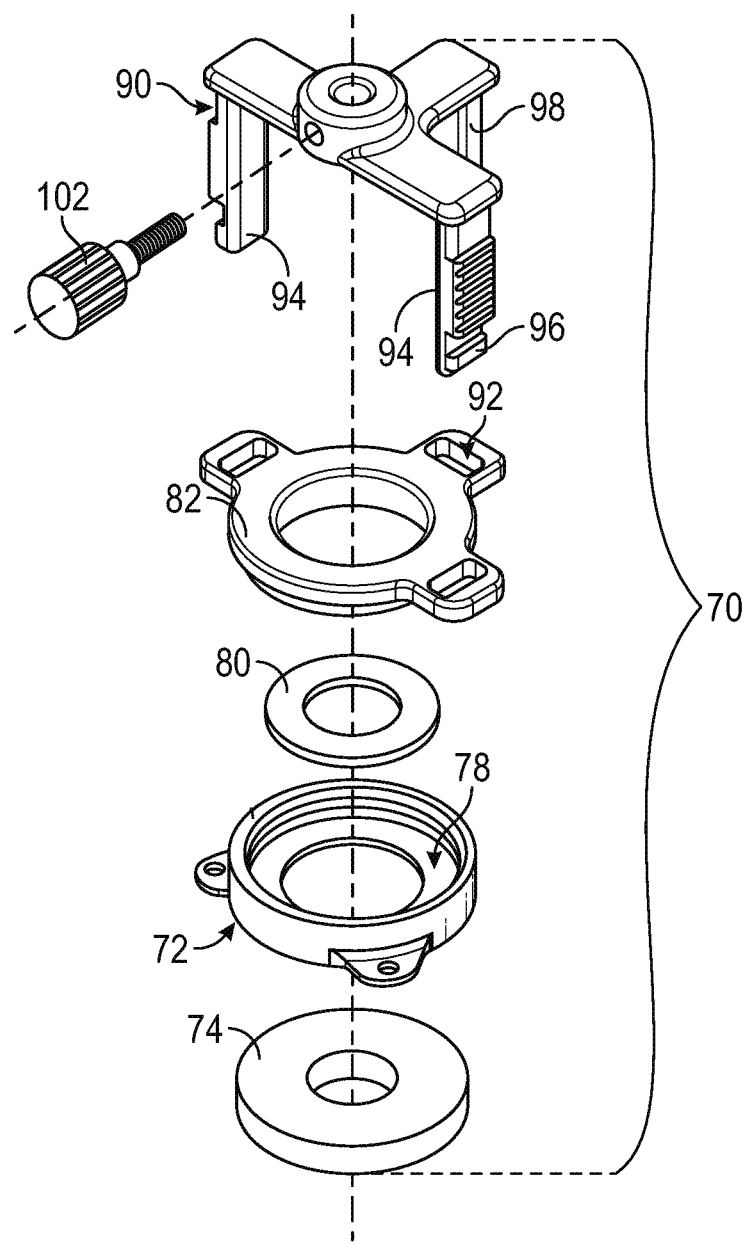
FIG. 8D is an exploded view of the locking assembly.

FIG. 8D shows a detailed schematic view of the different elements of the locking assembly 70. The annular base 72 includes a flange with a recess below 78. The cushion 74 is attached to the rigid or semi-rigid flange 78 within the recess below unit 72. The cushion 74 may be constructed of a conformal material, such as closed cell silicone foam approximately 3 to 12 mm thick, with an outer diameter preferably between 18 and 36 mm. The cushion 74 allows a compressible interface on the patient's head to create a minimal invasive interface that is sealed. The expandable access sheath is attached to the cushion, the annular base or the washer. The annular base 72 may have features, such as rings or holes, on its outer perimeter to allow for suture or tacking attachments to the head. Alternatively, the annular base unit may attach to an external fixation device such as a autoclavable holding system.

Housed within the flange 78 of the annular base 72 is a rigid or semi rigid washer 80. The washer is sized to be smaller than the circular diameter of the flange. This allows the washer to act as a disk that shifts freely to eccentric positions relative to the flange and the cushion FIG. 12B. The eccentric positioning relative to the flange and base allows locking the expansion tube 42 into various positions offset from the center line of the locking assembly. The washer 80 may be made of stainless steel or polycarbonate or other similar materials and maybe 1.5 to 3 mm thick. The washer 80 may be replaced by an equivalent element, such as a tube, cube or sphere set up to similarly shift within a recess of a base 72 when the locking assembly is unlocked.

Also in threaded attachment to the annular base 72 is a cap 82 which can be twisted relative to the flange thereby decreasing the height of the circular recess. Twisting the cap compresses the cap against the washer 80, holding it in whatever inline or eccentric position it has taken relative to the annular base unit and cushion. In alternative embodiments, rather than twisting the cap to compress the washer, the cap can be pressed down to compress the washer 80 or any other means of compression.

The twistable cap 82 also has one or more slots 92 for releasable attachment of a stylet stabilizing assembly 90. In this embodiment, the stylet stabilizing assembly consists of two flexible standoff legs 94 terminating in barbs 96 that interlock with slots 92 on the cap 82. There is additionally a third standoff 98 that is static relative to the assembly and allows for additional stability of the stylet stabilizing assembly 90. In this embodiment, there is a thumbscrew 102 for secure but releasable attachment of the stylet 50.

Figure 9:
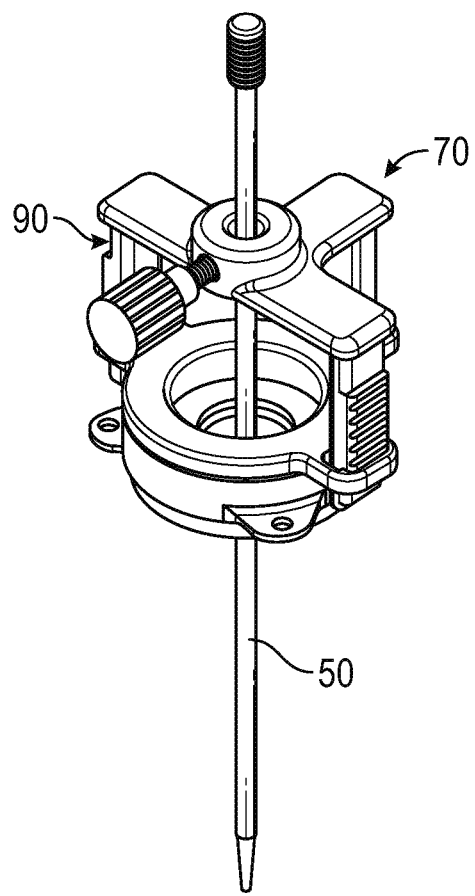
FIG. 9 is a top perspective view of the locking assembly with the stylet in place and with the sheath removed for purpose of illustration.

FIG. 9 shows an optional stylet 50 or navigation probe that can be introduced and positioned at a variety of extending lengths. Once the stylet or probe is positioned relative to the assembly 90 it can be releasable locked in place by the thumbscrew.

Figure 10A:
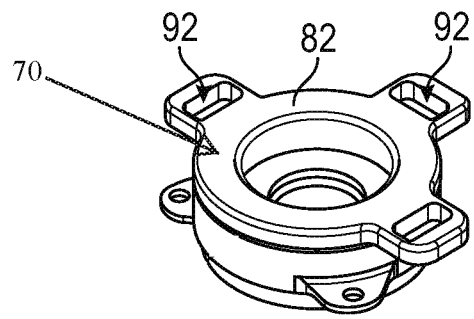
FIG. 10A is a top perspective view of the base unit of the locking assembly with the stylet stabilizing assembly removed.

FIG. 10A shows the locking assembly with the stylet and the stylet stabilizing assembly removed.

Figure 10B:
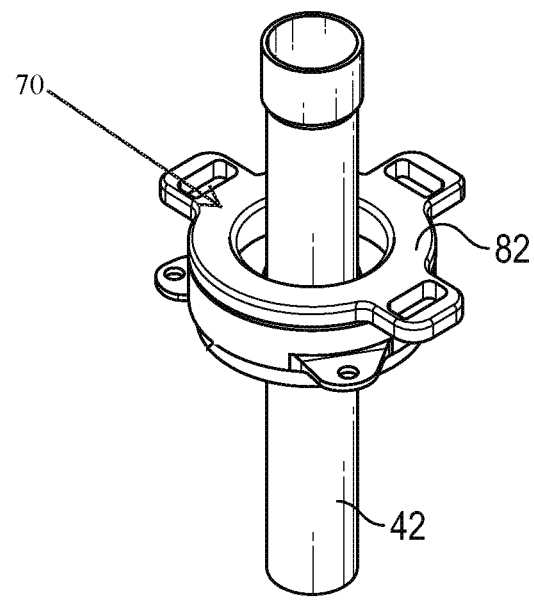
FIG. 10B shows an expansion tube placed in the locking assembly.

FIG. 10B shows the locking assembly with the stylet and stabilizing assembly removed, allowing the expansion tube 42 to be inserted in the locking assembly 70. The radially expanded access sheath is not shown for clarity of illustration purposes. The expansion tube is inserted through the washer 80, flange 78, cushion 74, and into the expansion sheath.

Figure 11C:
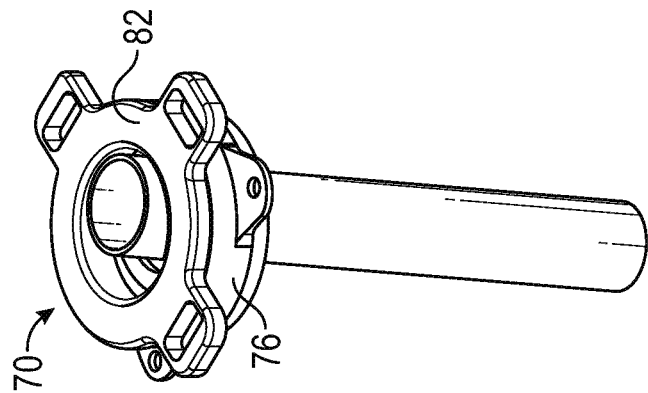
FIG. 11C shows the cap of the locking assembly rotated to cause it to compress the washer of the locking assembly, maintaining a locked angulated position.
Figure 11B:
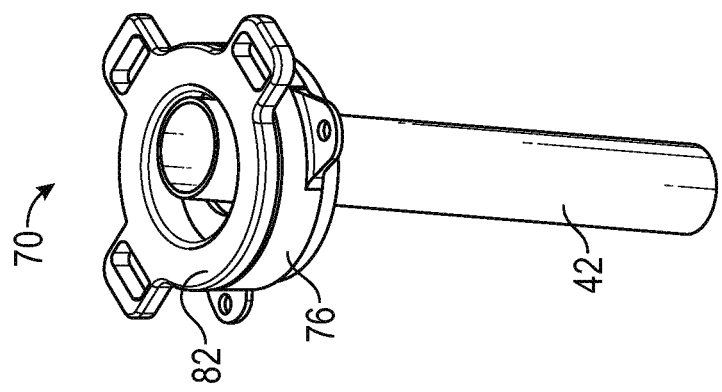
FIGS. 11A and 11B are top perspective views showing the expansion tube placed in the base unit in a straight manner and then angulated manner, respectively, with the locking assembly maintaining the position of the expansion tube.
Figure 11A:
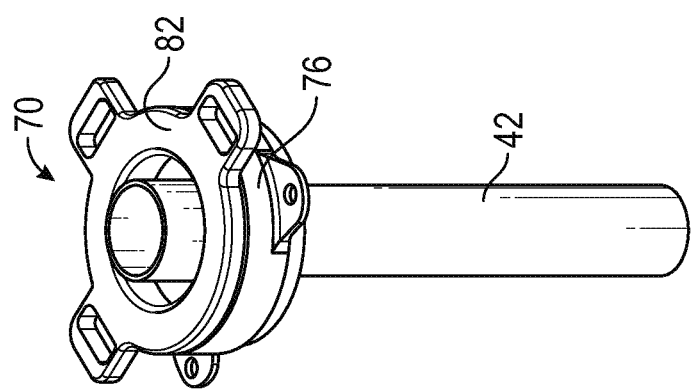

Once placed, the access sheath 40 can be shifted or offset horizontally as shown in FIGS. 11A, 11B and 11C. If the physician desires to maintain the positioning of the expansion tube 42, they twist the cap 82 relative to the annular base 72 to create a compression on the washer.

Figure 12A:
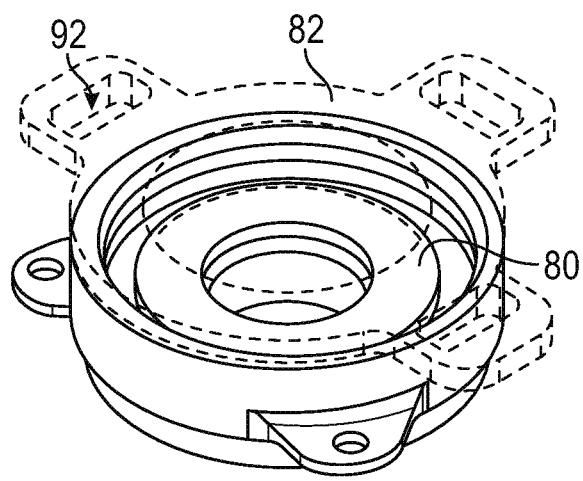
FIG. 12A is a top perspective view of the flange, washer and cap of the locking assembly in a first position, with FIG. 12B showing it in a second position.
Figure 12B:
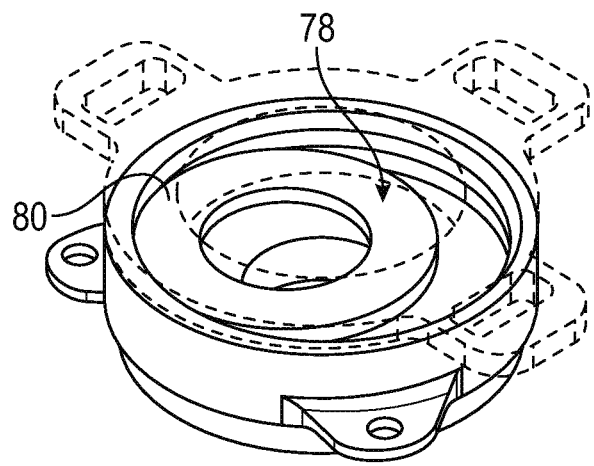

FIG. 12A and FIG. 12B. shows the washer 80 in two different locations relative to the flange 78 with compression from the twistable cap 82. With the expansion tube 40 centered in the flexible inner diameter of the cushion and the washer at an eccentric location, the expansion tube will be maintained by two contact locations at a slight misalignment relative to the neutral longitudinal axis of the system. This defines and maintains an angular position of the expansion tube and radially expanded access sheaths.

Additionally, the cap 82 can be twisted in the alternate direction to release compression on the washer. In this way, the angulation can be released and the sheath repositioned or placed in an alternative locked configuration. The twist and compression be made to partially compress the washer allowing dynamically locked angulation. This angulation may be locked well enough to maintain angular position in the absence of an overcoming positioning force, but also allow the user to apply an angulation by overcoming the dynamic interlock. Other techniques besides screw threads may be used to allow the cap 82 to lock onto and temporarily unlock from the base 72. For example, levers, cams, clamps, ratchet and bayonet fittings, etc. may optionally be used.

FIG. 13A-13E show an alternate embodiment 110 with a different expansion sheath and stylet stabilizing assembly.

The braided access sheath described previously is useful in that it expands in a radial fashion that propagates symmetrically as the expansion tube 42 is introduced. A drawback of that construction may be that there is a corresponding reduction in length as the braid expands. An alternate embodiment is constructed of a material such as a polymer sleeve, that expands radially but without significant reduction in length.

Consider an radially dilating access sheath made of a polymer preferably of a thickness between 0.08 mm and 0.4 mm. The access sheath when laid flat as a circular sleeve has a circular diameter of approximately 12 mm or at least the cross sectional circular diameter of the expansion tube 42.

FIG. 13A shows a radially dilating access sheath 112 configured from a different material with comparable function. The polymer expansion sheath 112 can be rolled in a scroll like fashion near the tip to create a low profile initial configuration which is attached to a locking hub assembly 110. Alternatively, it can be folded in flutes that are rolled in a circular fashion to create a low profile. It is used in a comparable fashion to the previously described embodiment.

Figure 13B:
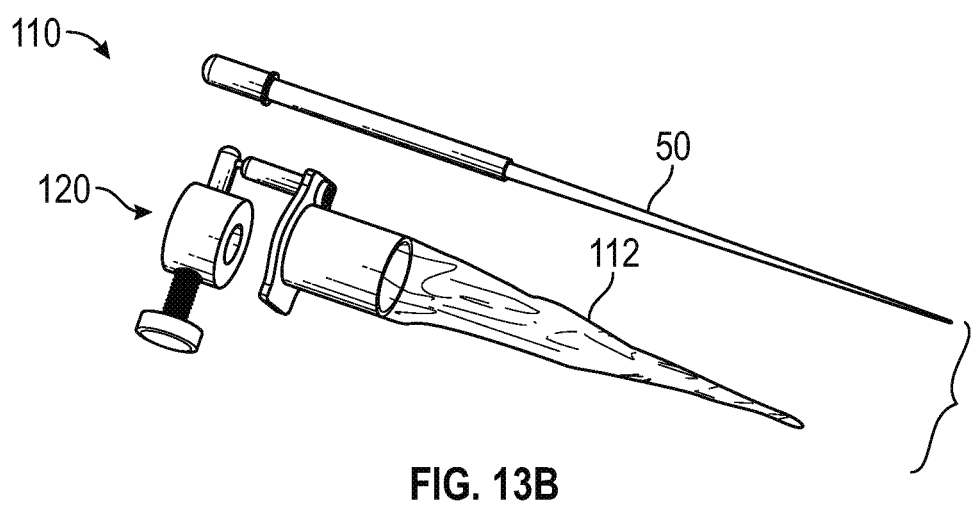
FIG. 13B shows the embodiment of FIG. 13A with the stylet removed.
Figure 13C:
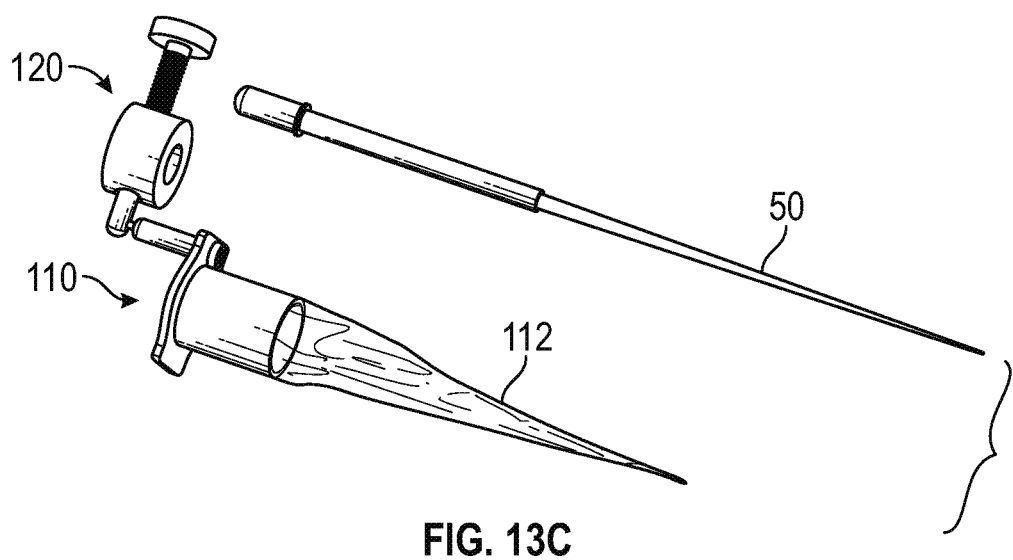
FIG. 13C shows the embodiment of FIGS. 13A and 13B now in a cleared configuration that allows placement of the expansion tube.

FIGS. 13A, 13B and 13C demonstrate an alternative locking assembly that does not require a stylet stabilization component. In this embodiment, the stylet stabilization component does not become removed from the stabilizing assembly.

FIGS. 13A and 13B show the locking assembly 110 in line with the access sheath 112. The stylet locking component 120 consisting of a holder 114 attached by a hinge 116 to a collar 118.

FIG. 13C shows the hinge articulated into a position where the stylet stabilization assembly is cleared from the path of the expansion tube 42.

Figure 13D:
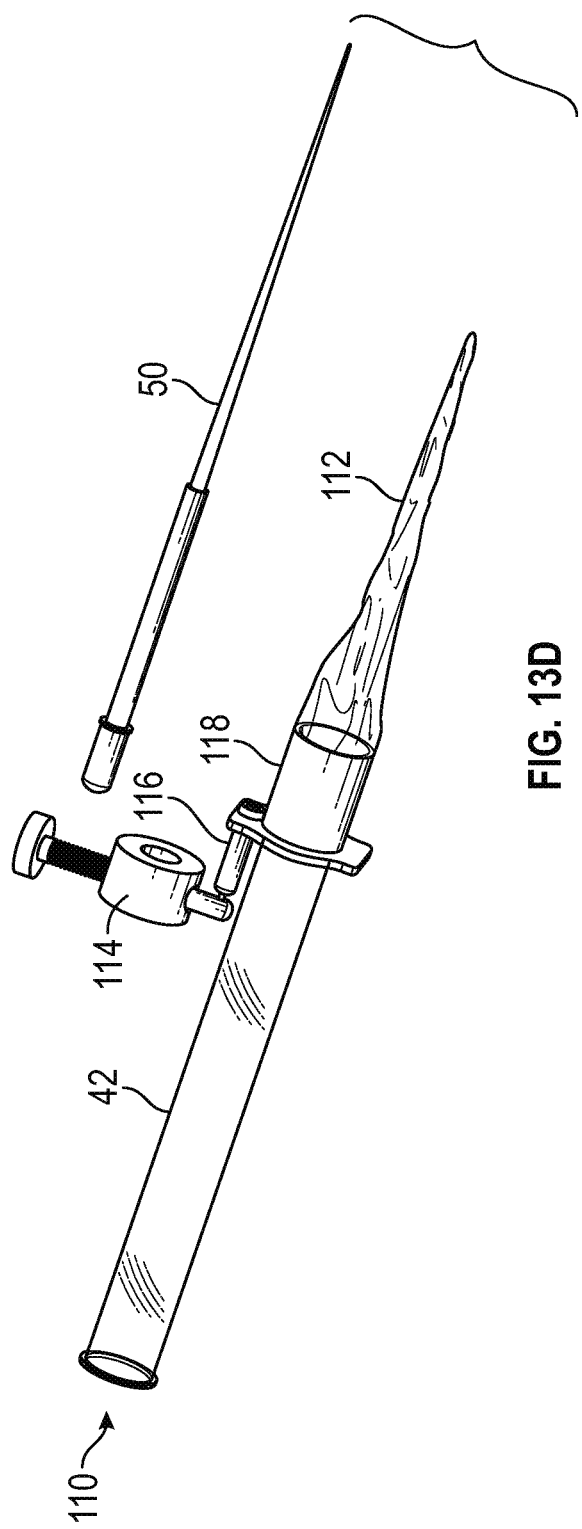
FIG. 13D shows introduction of the expansion tube in the embodiment of FIG. 13C.
Figure 13E:
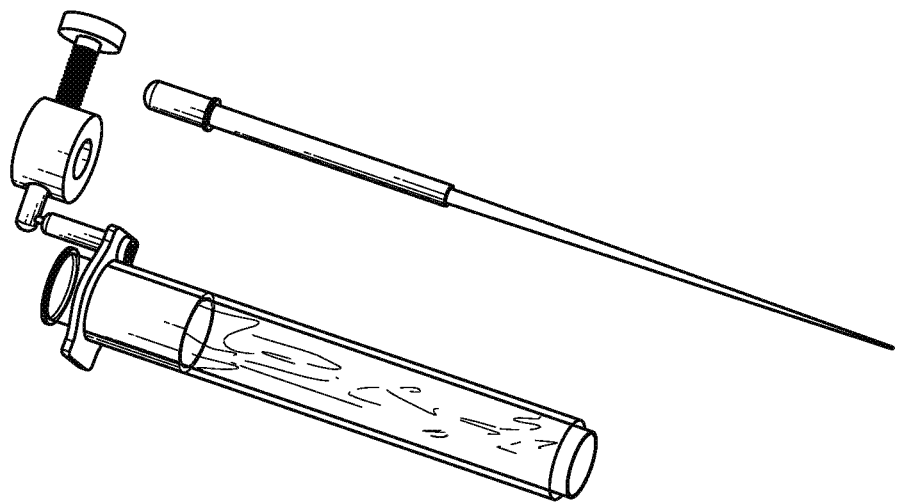
FIG. 13E shows the expansion tube placed causing the folded thin polymer access sheath to be deployed.

FIG. 13D shows the expansion tube inserted with the locking assembly cleared from the path. The stylet locking component 120 consists of a holder 114 attached by a hinge 116 to a collar 118. The benefit of this configuration is the locking assembly does not decouple preventing misplacement and makes components conveniently available.

As described above, a clinical benefit is that the locking assembly can be unlocked to allowed the expansion tube to be relocated into alignment with a different area of a surgical site, and then relocked into position, without changing the position of the locking assembly on the head of the patient. That is, the flexible tubular braided sheath cooperates with a stabilizing assembly which allows the flexible braided sheath to lock in different angular locations from a fixed reference point.

The proximal end of the sheath may be attached (via adhesives, etc.) to the cushion 74, with the cushion 74 attached to the base 72. In use, for example for surgery of a brain tumor, a stylet or other neuro-navigation device may first be inserted into the head of the patient to establish the position of the surgical site. The stylet is then withdrawn. The locking assembly 70 is then secured in place on the head, via suturing through the slots 92 to skin, or via a rigid frame around or attached to the head, with the sheath 40 projecting into the surgical opening.

The expansion tube 42 is then inserted through the washer 80 of the locking assembly 70 and into the sheath 40. This causes the sheath 40 to expand radially outward. The locking assembly 70 is in the locked configuration, i.e., with the cap 82 tightened onto the base 72, locking the washer 80, and correspondingly the expansion tube 42, into a fixed position. One or more surgical tools is inserted through the expansion tube 42 to access a first position of the surgical site, e.g., a first area of the tumor. After surgery of the first area, the locking assembly 70 is unlocked by temporarily unscrewing the cap 82. The washer 80 is then free to move in any direction radially. This allows the expansion tube to shift in the lateral and longitudinal directions. The expansion tube 42 is shifted or offset horizontally into a desired second position, e.g., so that the expansion tube 42 is now aligned over a second area of the tumor. The locking assembly 70 is re-locked by re-tightening the cap. Surgery of the second area is then performed, again by inserting one or more surgical tools through the expansion tube 42. As a result, the locking assembly allows the surgical tools to access different locations of the surgical site, while the locking assembly remains fixed in place on the head.

Typically, the diameter of the opening through the skull is smaller than horizontal shift range of the washer 80 (the shift range equal to one half of the diameter of the recess 78 minus the outside diameter of the washer 80). As a result, depending on the geometry of the specific locking assembly 70 and other factors, the angle of expansion tube 42 relative to the skull may change when expansion tube is shifted between the first and second positions as described above.

The distal end of the expansion tube is able to move in two axes when the locking assembly is unlocked, and the distal end of the expansion tube substantially immovable when the locking assembly is locked. Substantially immovable means not inadvertently movable when applying the nominal hand forces used when performing.

In one embodiment a surgical sheath system includes a flexible tubular braided sheath which is radially expandable, and an expansion tube insertable into the sheath to radially expand the sheath. A locking assembly includes expansion tube shift means, for allowing the expansion tube to shift horizontally when the locking assembly is unlocked. The expansion tube shift means may be provided as a cap threaded onto a flange, with a washer contained in a recess in the flange, the recess having an inside diameter greater than an outside diameter of the washer.

A method for surgery of the head includes inserting a distal end of a flexible conical braided sheath through an opening in the head of a patient; expanding the braided sheath radially outward by advancing a substantially rigid tube into a back end of the sheath causing the sheath to expand radially outward. The sheath may have an elastomer coating, and an outer diameter of 8 to 18 mm.

Thus, a novel access sheath, locking assembly and related methods have been shown and described. Various changes and substitutions may of course be made without departing from the spirit and scope of the invention. The invention, therefore, should not be limited except by the following claims and their equivalents.

The invention claimed is:

1. A sheath kit for brain surgery comprising:
   a base including a locking assembly movable to a locked position and to an unlocked position, the locking assembly having elements for attachment to the head of a patient;
   a radially expandable flexible sheath attached directly or indirectly to the base; and
   an expansion tube insertable through the locking assembly into the sheath to radially expand the sheath, the locking assembly holding the expansion tube in fixed position when the locking assembly is in the locked position.

2. The sheath kit of claim 1, wherein the flexible sheath is a tubular braided sheath.

3. The sheath kit of claim 1, wherein a distal end of the expansion tube is able to move in two axes when the locking assembly is unlocked, and wherein the distal end of the expansion tube is substantially immovable when the locking assembly is locked.

4. The sheath kit of claim 1, wherein the base comprises a rigid circular base.

5. The sheath kit of claim 1, wherein the sheath is attached to a resilient cushion and the resilient cushion is attached to the base.

6. The sheath kit of claim 1, wherein the locking assembly includes a cap threaded onto a flange, with a washer contained in a recess in the flange, the recess having an inside diameter greater than an outside diameter of the washer.

7. A surgical sheath system, comprising:
   a flexible tubular braided sheath which is radially expandable;
   an expansion tube insertable into the sheath to radially expand the sheath;
   a locking assembly including a cap threaded onto a flange, with a washer contained in a recess in the flange, the recess having an inside diameter greater than an outside diameter of the washer.

8. The system of claim 7 further including a cushion attached to a bottom surface of the flange.

9. The system of claim 7 further including a stylet stabilizing assembly releasably attached to the cap, via one or more legs, and a central opening coaxial with recess.

10. The surgical sheath system of claim 9 further including a stylet extending through the central opening, and a locking screw in the stylet stabilizing assembly engageable against the stylet to lock the stylet against longitudinal movement.

11. The system of claim 7, wherein an inside diameter of an opening through the washer is 0.1 mm to 3 mm larger than an outside diameter of the expansion tube, and wherein an inside diameter of the recess is 2 mm to 40 mm larger than the outside diameter of the washer.

12. The system of claim 7 further including slots or openings in the cap for securing the cap to a surgical site.

13. The system of claim 7, wherein the washer has a diameter 10 to 50% less than the diameter of the recess, to allow the washer to be positioned eccentrically relative to the cap and/or the flange.

14. A surgical sheath system for use in surgery of the head of a patient, comprising:
   a radially expandable flexible sheath;
   a stabilizing assembly including a stylet holder attached to a collar by a hinge;
   a locking assembly on or in the collar, the locking assembly movable to a locked position and to an unlocked position and having elements for attaching it to the head of the patient;
   a first end of the sheath attached to the collar;
   an expansion tube insertable into the sheath to radially expand the sheath;
   the stabilizing assembly pivotal to a first position to allow inserting the expansion tube into the sheath, and to a second position for holding a stylet projecting into the sheath; and
   the locking assembly allowing the expansion tube to shift horizontally when in an unlocked configuration.

* * * * *